US012810395B2

(12) United States Patent
Oh et al.

(10) Patent No.: US 12,810,395 B2
(45) Date of Patent: Nov. 24, 2026

(54) IMAGE PROCESSING METHOD AND APPARATUS FOR GRID ARTIFACT REMOVAL IN X-RAY IMAGES

(71) Applicant: LG ELECTRONICS INC., Seoul (KR)

(72) Inventors: Jaehyun Oh, Seoul (KR); Sunghyun Kim, Seoul (KR); Hyewon Im, Seoul (KR); Jongsang Yoo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 279 days.

(21) Appl. No.: 18/698,708

(22) PCT Filed: Jul. 21, 2022

(86) PCT No.: PCT/KR2022/010685
§ 371 (c)(1),
(2) Date: Apr. 4, 2024

(87) PCT Pub. No.: WO2023/058858
PCT Pub. Date: Apr. 13, 2023

(65) Prior Publication Data

US 2024/0404021 A1 Dec. 5, 2024

(30) Foreign Application Priority Data

Oct. 5, 2021 (KR) ........................ 10-2021-0131463

(51) Int. Cl.
*G06T 5/70* (2024.01)
*A61B 6/00* (2024.01)
*G06T 5/20* (2006.01)

(52) U.S. Cl.
CPC .............. *G06T 5/70* (2024.01); *A61B 6/5258* (2013.01); *G06T 5/20* (2013.01); *G06T 2207/10116* (2013.01); *G06T 2207/30004* (2013.01)

(58) Field of Classification Search
CPC ... G06T 5/70; G06T 5/20; G06T 2207/10116; G06T 2207/30004; G06T 2207/20056;
(Continued)

(56) References Cited

U.S. PATENT DOCUMENTS 5,598,481 A 1/1997 Nishikawa et al.
6,269,176 B1 * 7/2001 Barski ........................ G06T 5/10 382/128
(Continued)

FOREIGN PATENT DOCUMENTS

EP 1 696 366 A1 8/2006
JP 7-299053 A 11/1995
(Continued)

OTHER PUBLICATIONS

International Search Report for PCT/KR2022/010685 mailed on Nov. 2, 2022.
(Continued)

*Primary Examiner* — Henok Shiferaw
*Assistant Examiner* — Dion J Satcher
(74) *Attorney, Agent, or Firm* — Birch, Stewart, Kolasch & Birch, LLP

(57) ABSTRACT

Discussed is an image processing method and device. An image processing method according to an embodiment can include obtaining an X-ray image, converting the obtained X-ray image into a frequency domain, detecting peak shape information from the converted X-ray image in the frequency domain, selecting a peak candidate region based on detected the peak shape information, determining whether
(Continued)

each selected peak candidate region is a grid peak and generating a peak map, filtering the converted X-ray image based on the generated peak map, converting the filtered X-ray image in the frequency domain into a spatial domain, and providing a domain converted X-ray image in the spatial domain.

18 Claims, 12 Drawing Sheets

(58) Field of Classification Search
CPC ....... G06T 5/10; A61B 6/5258; A61B 6/4291; A61B 6/5205; A61B 6/5282; A61B 6/00
USPC .......................................................... 382/132
See application file for complete search history.

(56) References Cited

U.S. PATENT DOCUMENTS

| | | | | |
|---|---|---|---|---|
| 6,333,990 | B1 * | 12/2001 | Yazici | G06T 5/70 382/132 |
| 7,479,969 | B2 * | 1/2009 | Behiels | G06T 7/12 382/128 |
| 7,826,682 | B2 | 11/2010 | Behiels et al. | |
| 10,297,010 | B2 | 5/2019 | Zhang et al. | |
| 2003/0152259 | A1 * | 8/2003 | Belykh | A61B 6/5252 382/280 |
| 2004/0202361 | A1 | 10/2004 | Evans et al. | |
| 2006/0233453 | A1 | 10/2006 | Behiels et al. | |
| 2011/0033101 | A1 * | 2/2011 | Foos | A61B 6/5252 382/132 |
| 2011/0122994 | A1 | 5/2011 | Grubsky et al. | |
| 2014/0050300 | A1 * | 2/2014 | Hasegawa | A61B 6/5258 378/62 |
| 2014/0363071 | A1 * | 12/2014 | Imai | A61B 6/4291 382/132 |
| 2015/0348290 | A1 | 12/2015 | Yi et al. | |
| 2016/0027153 | A1 | 1/2016 | Eun et al. | |
| 2017/0140203 | A1 * | 5/2017 | Naito | G06V 10/431 |
| 2017/0270640 | A1 | 9/2017 | Zhang et al. | |
| 2017/0324885 | A1 * | 11/2017 | Ochiai | G06K 15/1878 |
| 2018/0005360 | A1 * | 1/2018 | Probel | G01V 5/045 |
| 2018/0068468 | A1 * | 3/2018 | Kawamura | G06T 5/70 |
| 2021/0137469 | A1 | 5/2021 | Zhao | |

FOREIGN PATENT DOCUMENTS

| | | |
|---|---|---|
| KR | 10-2015-0139375 A | 12/2015 |
| KR | 10-2016-0012559 A | 2/2016 |
| KR | 10-2020-0133361 A | 11/2020 |

OTHER PUBLICATIONS

Barski et al., "Characterization, detection and suppression of stationary grids in digital projection radiography imagery," SPIE Conference on Image Display, vol. 3658, Feb. 1999, pp. 502-519.
Belykh et al., "Antiscatter stationary grid artifacts automated detection and removal in projection radiography images," Proceedings of SPIE, vol. 4322, 2001, pp. 1162-1166.
Varghese et al., "Adaptive Gaussian notch filter for removing periodic noise from digital images," IET Image Processing, vol. 14, Issue 8, 2020, pp. 1529-1538.

* cited by examiner (a)

(b)

(a) (b)

(c) (d)

IMAGE PROCESSING METHOD AND APPARATUS FOR GRID ARTIFACT REMOVAL IN X-RAY IMAGES

CROSS REFERENCE TO RELATED APPLICATIONS

This application is the National Phase of PCT International Application No. PCT/KR2022/010685, filed on Jul. 21, 2022, which claims priority under 35 U.S.C. 119 (a) to Patent Application No. 10-2021-0131463, filed in the Republic of Korea on Oct. 5, 2021, all of which are hereby expressly incorporated by reference into the present application.

DISCLOSURE

Technical Field

The present disclosure relates to image processing, and more specifically, to an image processing method and device for removing artifacts included in an obtained image.

Background

An X-ray medical diagnostic device is a device that photographs the inside of the human body for radiological examination. Typically, medical diagnostic devices used in hospitals detect X-rays emitted from an X-ray tube through an X-ray detector when they pass through an object such as an animal or a patient's body.

These X-ray medical diagnostic devices are mainly used to obtain medical images of the chest, head, digestive tract, spine, and injured regions of the human body.

Meanwhile, images acquired through X-ray medical diagnostic devices usually include artifacts and processing for these artifacts is required.

However, according to related X-ray medical diagnostic devices, it was difficult to effectively respond to various artifacts included in the acquired images, so there were limitations in providing images of the desired quality. These limitations can cause problems such as reading errors when reading acquired images, so a solution is required.

Technical Object

The technical object of the present disclosure is to provide a method and device for processing images to improve image quality by effectively processing them while preventing or minimizing false detection of artifacts included in images obtained from an X-ray device.

Technical Solution

An image processing method according to an embodiment of the present disclosure includes obtaining an X-ray image; converting the obtained X-ray image into a frequency domain; detecting peak shape information from the converted X-ray image in the frequency domain; selecting a peak candidate region based on the peak shape information; determining whether each selected peak candidate region is a grid peak and generating a peak map; filtering based on the generated peak map; converting the filtered X-ray image in the frequency domain into a spatial domain; and providing a converted X-ray image in the spatial domain.

An image processing device according to an embodiment of the present disclosure includes a data receiver configured to obtain an X-ray image; a first converter configured to convert the obtained X-ray image into a frequency domain; a data processor configured to: detect peak shape information from the converted X-ray image in the frequency domain, select a peak candidate region based on the peak shape information, determine whether each selected peak candidate region is a grid peak and generate a peak map, and filter based on the generated peak map; a second converter configured to convert the filtered X-ray image in the frequency domain into a spatial domain; and a controller configured to control the converted X-ray image in the spatial domain to be provided.

Effects of the Invention

There is an effect of providing a diagnostic image while minimizing loss of the original image by preventing or minimizing erroneous detection of grid artifacts for various grid specifications according to an embodiment of the present disclosure.

BEST MODE

Hereinafter, embodiments related to the present invention will be described in more detail with reference to the drawings. The suffixes "module" and "part" for components used in the following description are given or used interchangeably only for the ease of preparing the specification and do not have distinct meanings or roles in themselves.

The present disclosure relates to image processing, and in particular, seeks to improve image quality of an X-ray image by removing artifacts included in the X-ray image, thereby increasing readability during reading.

In this specification, the term 'artifact' as described herein encompasses not only mere defects but also those arising from factors such as a grid, etc., which will be described later. In other words, for instance, naming a part other than bones or body images of the subject in X-ray images as an artifact is not limited to thereto.

Meanwhile, in the present specification, artifacts mainly occurring due to the grid, that is, grid artifacts, are called 'peak' or 'grid peak.' In the present disclosure, suppression or filtering of grid artifacts is specified, but is not limited to thereto. In other words, the peak or grid peak is generated by the grid and can mean point that appear periodically at regular intervals for all frequencies. That is, the present disclosure does not process all grid artifacts, but removes peaks that periodically appear for all frequencies within a range that prevents or minimizes damage to the original X-ray image.

Figure 2:
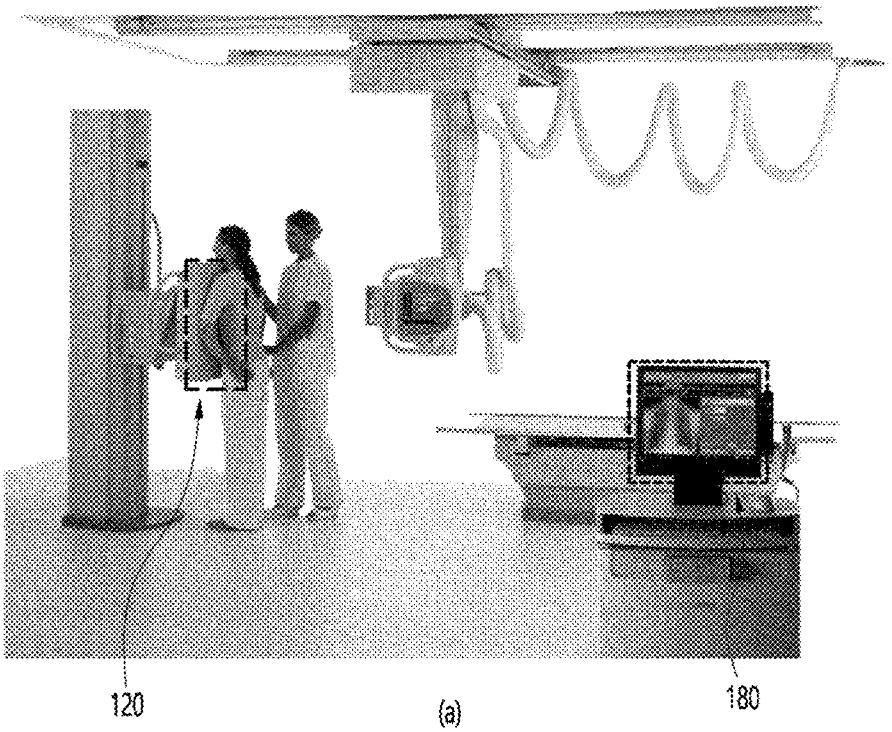
FIG. 2, including (a) and (b), illustrates an example of the image processing system of FIG. 1 that is actually implemented.
Figure 2:
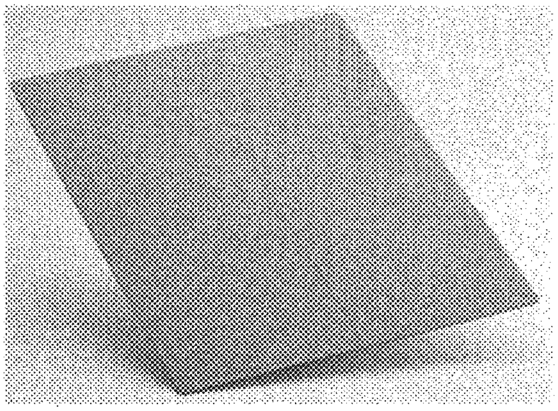

The 'grid' described in this specification can have a shape as shown in, for example, (b) of FIG. 2, and transmitting material and blocking material are arranged at a certain thickness and interval. During X-ray imaging, it serves as a means to increase diagnostic accuracy by lowering contrast of the X-ray images and eliminating scattered radiation, which cause deterioration in the quality of imaging using radiation such as X-rays.

The 'ruler' described in this specification refers, for example, to something (810) shown in (a) of FIG. 8 and is for convenience in reading X-ray images later. Therefore, it is generally preferrable to process the ruler so that it is not suppressed or filtered during the X-ray image processing process, so that it can be used as a reference for reading using the result.

Figure 1:
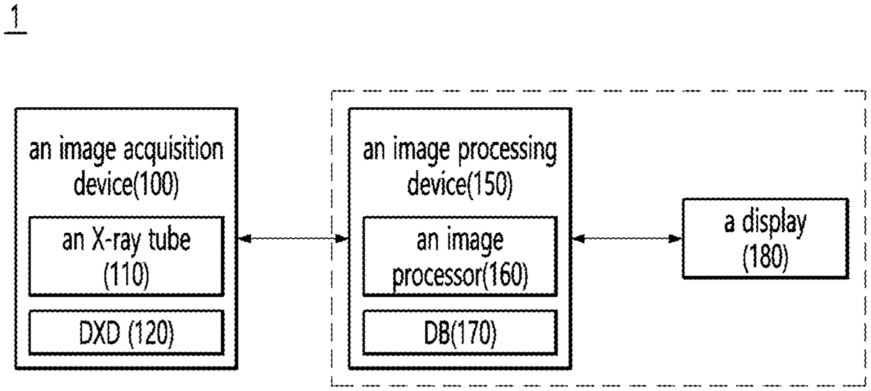
FIG. 1 is a schematic diagram of an image processing system according to an embodiment of the present disclosure.

FIG. 1 is a schematic diagram of an image processing system (1) according to an embodiment of the present disclosure.

FIG. 2 illustrates an example of the image processing system (1) of FIG. 1 that is actually implemented.

Figure 3:
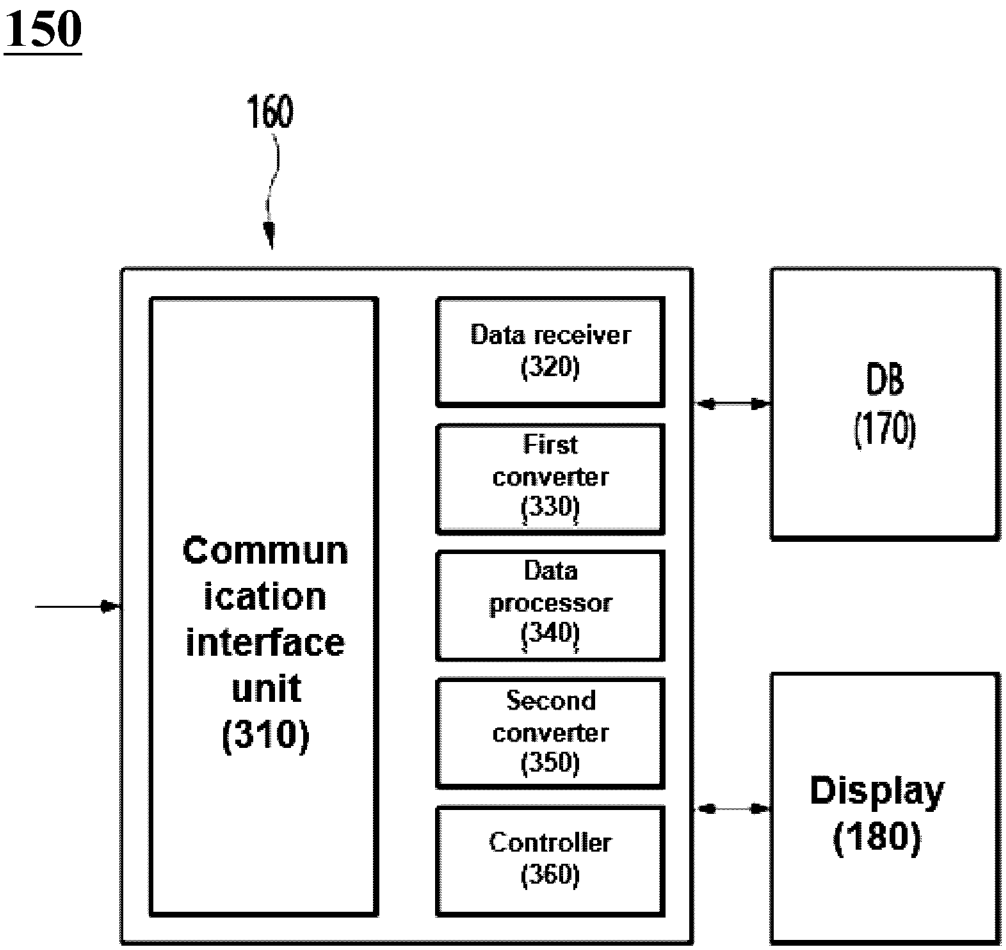
FIG. 3 is a block diagram of an image processing device according to an embodiment of the present disclosure.

FIG. 3 is a block diagram of an image processing device (150) according to an embodiment of the present disclosure.

Figure 8:
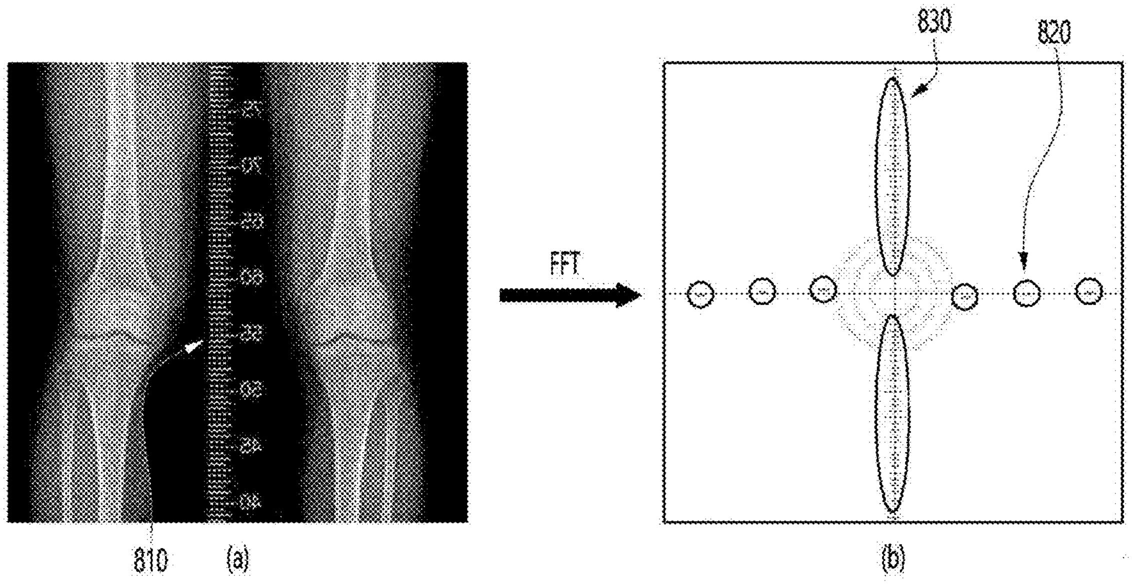
FIG. 8, including (a) and (b), is a diagram illustrating the conversion of an original X-ray image including a ruler into a frequency domain according to an embodiment of the present disclosure.

FIG. 8 is a diagram illustrating the conversion of an original X-ray image including a ruler (810) into the frequency domain according to an embodiment of the present disclosure.

Figure 9:
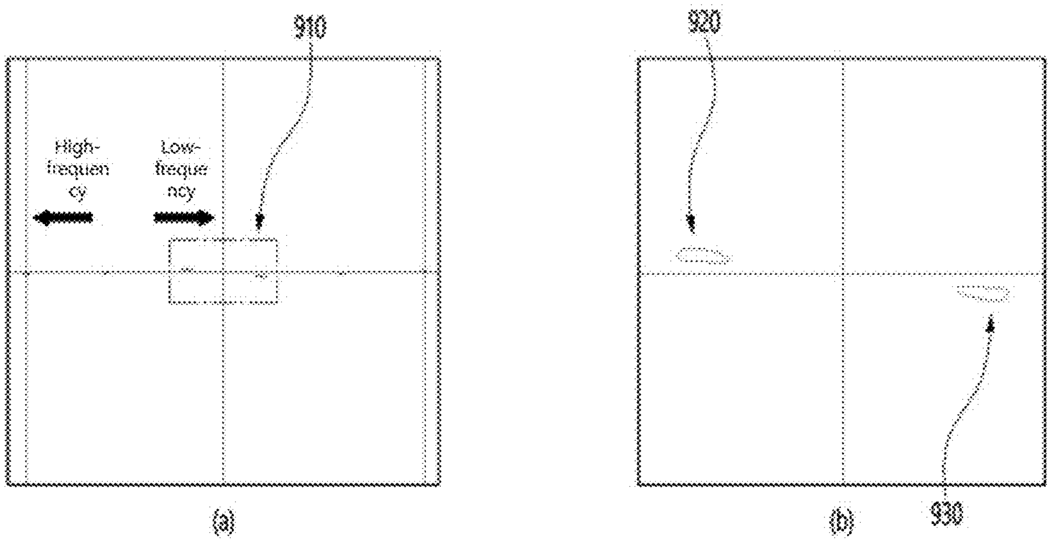
FIG. 9, including (a) and (b), is a diagram illustrating an image of a frequency domain including abnormal grid peaks according to an embodiment of the present disclosure.

FIG. 9 is a diagram illustrating a frequency domain image including abnormal grid peaks (920, 930) according to an embodiment of the present disclosure.

Figure 10:
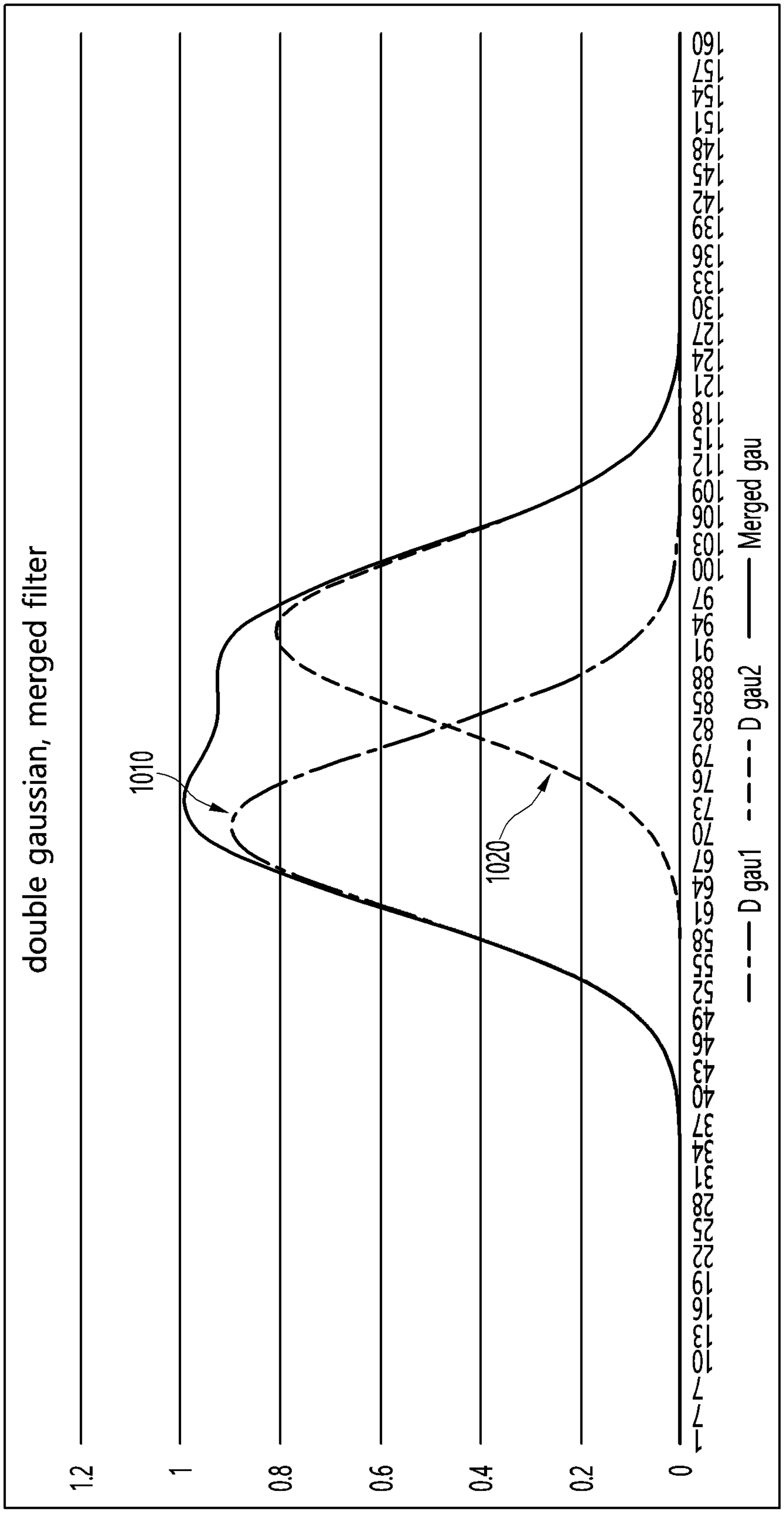
FIG. 10 is a graph illustrating a filtering operation according to an embodiment of the present disclosure.

FIG. 10 is a graph illustrating a filtering operation according to an embodiment of the present disclosure.

Figure 11:
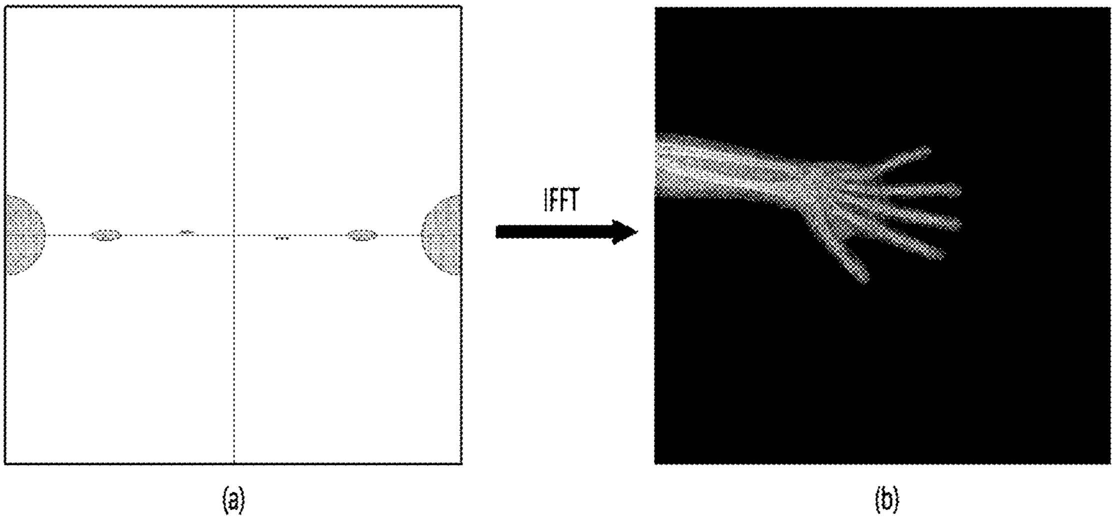
FIG. 11, including (a) and (b), is a diagram illustrating the inverse conversion of a frequency domain image from which grid peaks have been removed into an original X-ray image according to an embodiment of the present disclosure.

FIG. 11 is a diagram illustrating the inverse conversion of a frequency domain image from which grid peaks have been removed into an original X-ray image according to an embodiment of the present disclosure.

Figure 12:
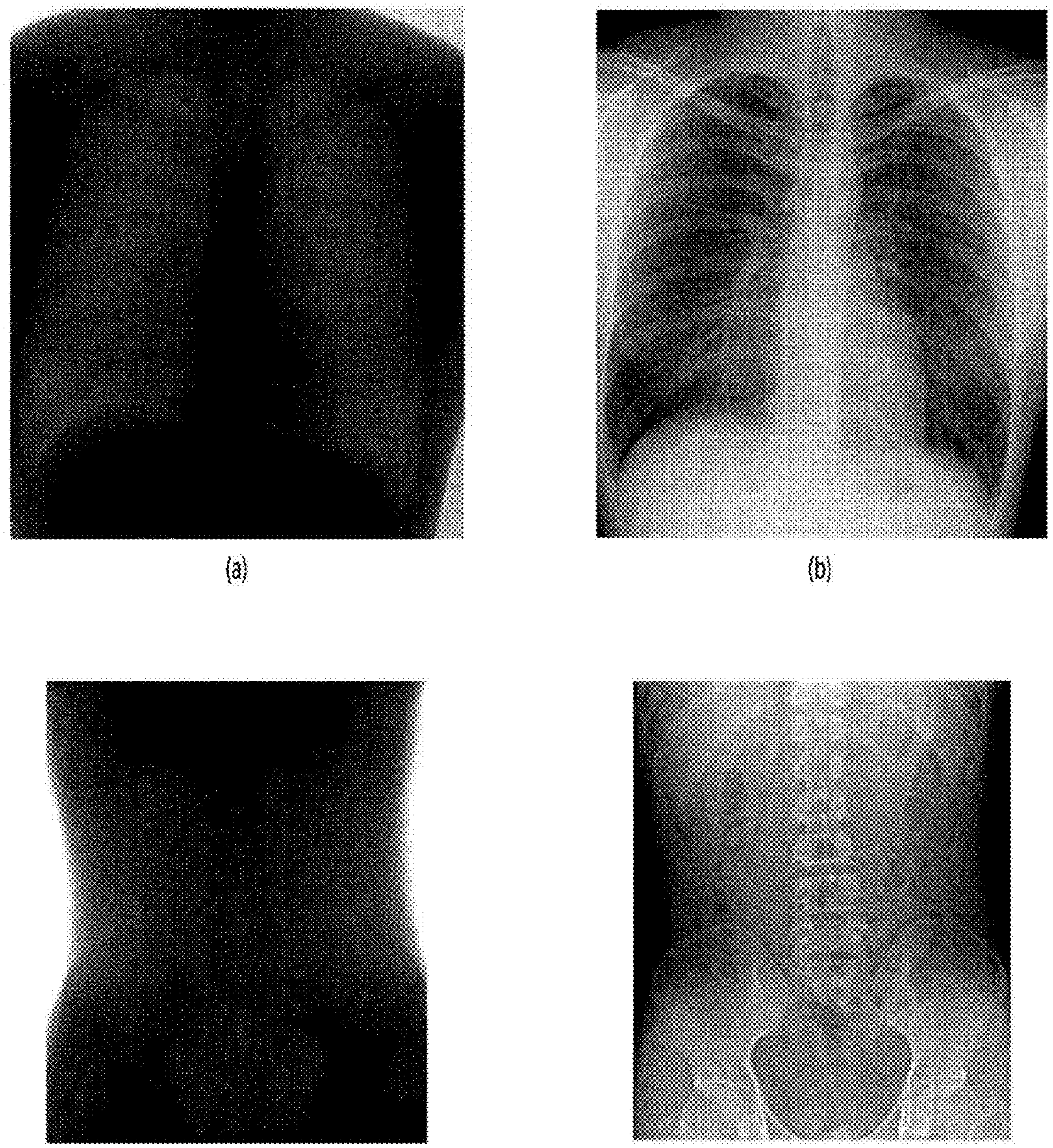
FIG. 12, including (a), (b), (c), and (d), is a diagram illustrating an original X-ray image and a post-processed image according to an embodiment of the present disclosure.

FIG. 12 is a diagram illustrating an original X-ray image and a post-processed image according to an embodiment of the present disclosure.

Referring to FIG. 1, the image processing system 1 can mainly include an image acquisition device 100, an image processing device 150, and an image output device 180.

The image processing system 1 or the image processing device 150 according to the present disclosure does not separate and process a high-frequency region and low-frequency region in a detection process and suppression process for artifacts, grid line artifacts are processed for all frequency domains. Therefore, according to the present disclosure, it is possible to respond to all grid specifications.

According to an embodiment, the image output device 180 can be a component of the image processing device 150.

The image acquisition device 100 can include an X-ray tube 110 and a digital X-ray detector (DXD) 120.

The X-ray tube 110 radiates X-rays to the subject to be photographed.

The digital X-ray detector 120 detects X-rays irradiated to the subject.

Meanwhile, referring to (a) of FIG. 2, the grid as shown in (b) of FIG. 2 can be positioned between the digital X-ray detector 120 and the object to be captured (e.g., human body).

However, if the grid is used, artifacts can occur, and if the artifacts caused by the grid are not processed, such as compensation or removal, the image quality of the obtained image can deteriorate, reducing readability. Thus, processing those can be considered essential. In the above, artifacts due to the grid can include, for example, grid line shadows, moire patterns, etc.

Meanwhile, in the present disclosure, processing of artifacts caused by a grid is specified as an example, but is not limited thereto. Meanwhile, in the present disclosure, in the process of processing the artifact, when a ruler that can be used when taking an X-ray is included, separate processing is required for the artifact due to the grid and the ruler image. Because, typically, it is desirable for ruler images to be included when providing processed image outputs.

The image acquisition device 100 can transmit the image detected through the digital X-ray detector 120 to the image processing device 150.

In this case, the image acquisition device 100 and image processing device 150 can perform data communication through a wired/wireless network.

Next, the image processing device 150 can process the X-ray image received through the image acquisition device 100 and provide it through the display 180.

Referring to FIGS. 1 and 3, the processor 160 can be implemented by including a communication interface unit 310, a data receiver 320, a first converter 330, a data processor 340, a second converter 350, and a controller 360.

The communication interface unit 310 can provide an interfacing environment for data communication with the image acquisition device 100.

The communication interface unit 301 may perform short-range communication with the image acquisition device 100. To this end, the communication interface unit 301 can support short-range communication using at least one technology among Bluetooth™, Bluetooth Low Energy (BLE), Radio Frequency Identification (RFID), Infrared Data Association (IrDA), Ultra Wideband (UWB), ZigBee, and NFC (Near Field Communication), Wi-Fi (Wireless-Fidelity), Wi-Fi Direct, and Wireless USB (Wireless Universal Serial Bus). This communication interface unit 310 can support wireless communication between the image acquisition device 100 and the wireless communication system, between the image processing device 150 and the display 180, or between the image processing device 150 and the network where the server is located.

The data receiver 320 can receive X-ray image data from the image acquisition device 100 through the communication interface unit 310.

The first converter 330 can convert X-ray image data received through the data receiver 320, that is, raw image data. At this time, the conversion refers to, for example, converting an input X-ray image such as in (a) of FIG. 7 or (a) of FIG. 8 into frequency-domain image data such as in (b) of FIG. 7 or (b) of FIG. 8. To this end, the first converter 330 can perform a 2D Fast Fourier Transform (FFT) transform operation.

The data processor 340 can perform an operation according to the present disclosure for removing artifacts based on the frequency domain image data converted through the first converter 330.

The second converter 350 can inversely transform the frequency domain image data from which artifacts have been removed in the data processor 340. That is, the second converter 350 can perform an IFFT (Inverse FFT) transform operation on the image data in the frequency domain in which artifacts have been processed such as in FIG. 11(*a*)(*a*) of FIG. 11 to generate image data in a spatial domain such as in FIG. 11(*b*)(*b*) of FIG. 11.

The controller 360 can control the overall operation of the processor 160. To this end, the controller 360 can control the operation of each component constituting the processor 160.

The database (DB) 170 can temporarily store received X-ray images. Unlike shown in FIG. 1, the database (DB) 170 does not necessarily need to be built into the image processing device 150, and can be located externally or remotely.

Referring to FIGS. 1 to 3, the display 180 can receive and output an X-ray image processed through the processor 160. In this case, the display 180 can be in the form of a fixed device such as a monitor, TV, or signage, or a mobile device such as a cell phone, a tablet PC, or a lap-top. According to an embodiment, the display 180 can be a dedicated device for output image according to the present disclosure.

Here, the display 180 is a wearable device capable of exchanging data with (or interoperating with) another display device, such as a smartwatch, smart glasses, a head-mounted display (HMD), or a mobile terminal such as a smartphone. The communication interface unit 310 can detect (or recognize) a wearable device capable of communication around the image processing device 150. Furthermore, if the detected wearable device is a device authenticated to communicate with the image processing device 150 according to the present disclosure, the controller 360 can transmit at least a portion of data processed by the image processing device 150 to a wearable device through the interface unit 310. Accordingly, a user of a wearable device can use data processed by the display device 100 through the wearable device.

Meanwhile, since the image processing system 1, the image acquisition device 100, or the image processing device 150 shown in FIGS. 1 and 3 are only an example of the present disclosure, some of the illustrated components can be integrated, added, or omitted depending on the specifications of the actually implemented system or device.

That is, as needed, two or more components can be combined into one component, or conversely, one component can be subdivided into two or more components. In addition, the function performed by each component is for explaining embodiments of the present disclosure, and the specific operations or devices do not limit the scope of the present disclosure.

The operation of the image processing system 1 of FIGS. 1 to 3 described above will be described in more detail referring to the attached drawings as follows.

Figure 4:
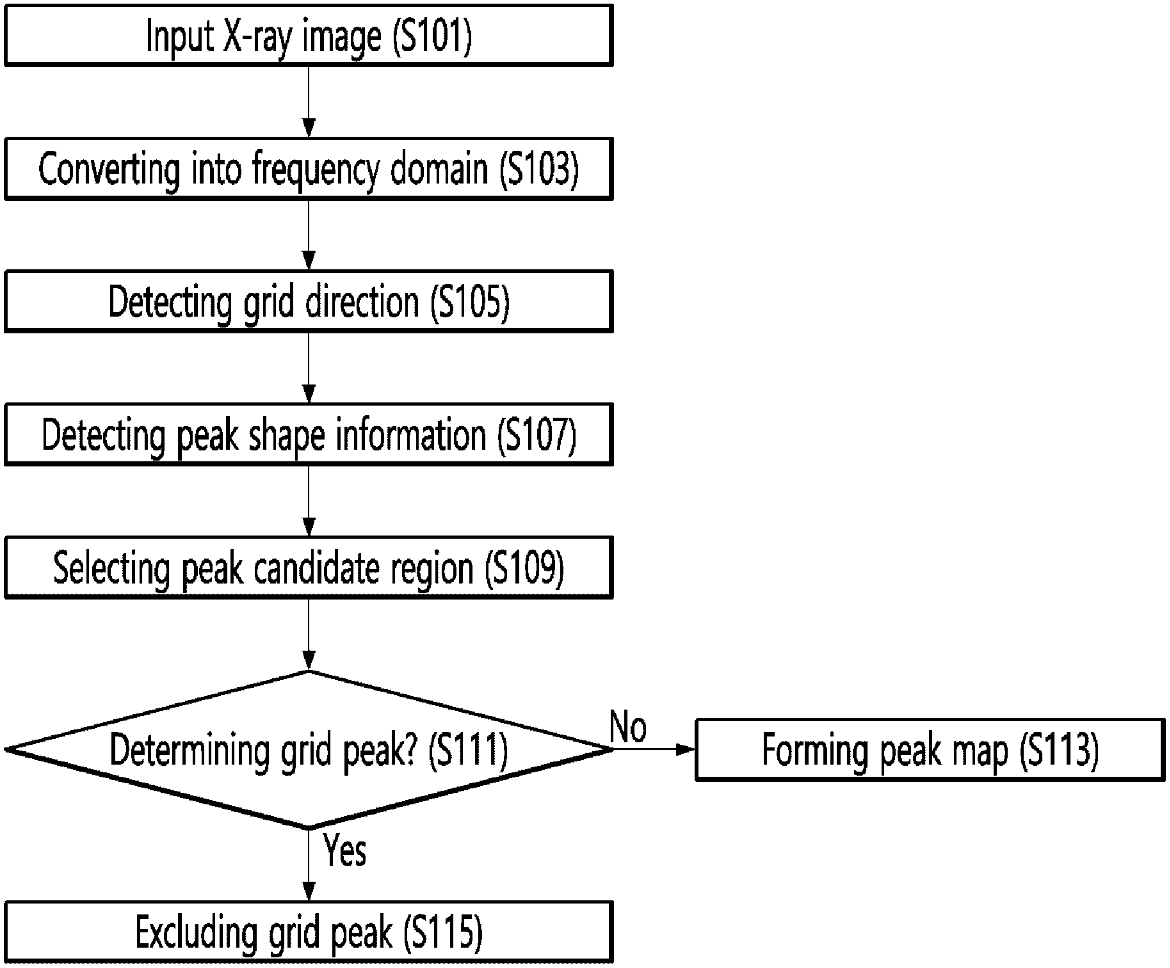
FIGS. 4 to 6 are flowcharts illustrating an image processing method according to an embodiment of the present disclosure.
Figure 5:
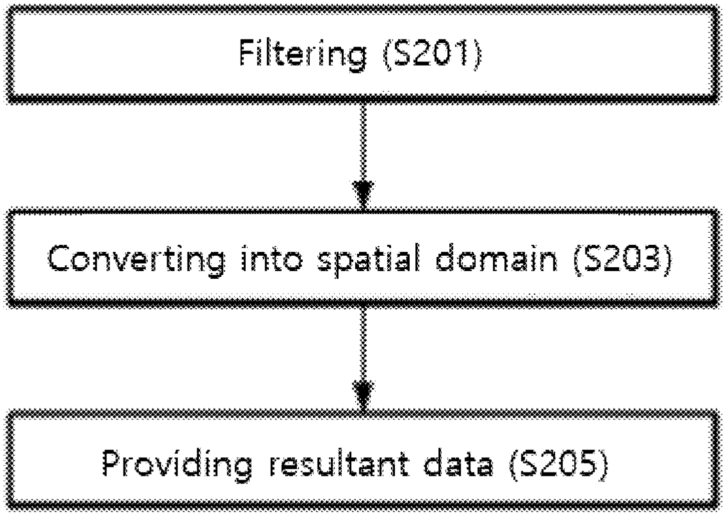
Figure 6:
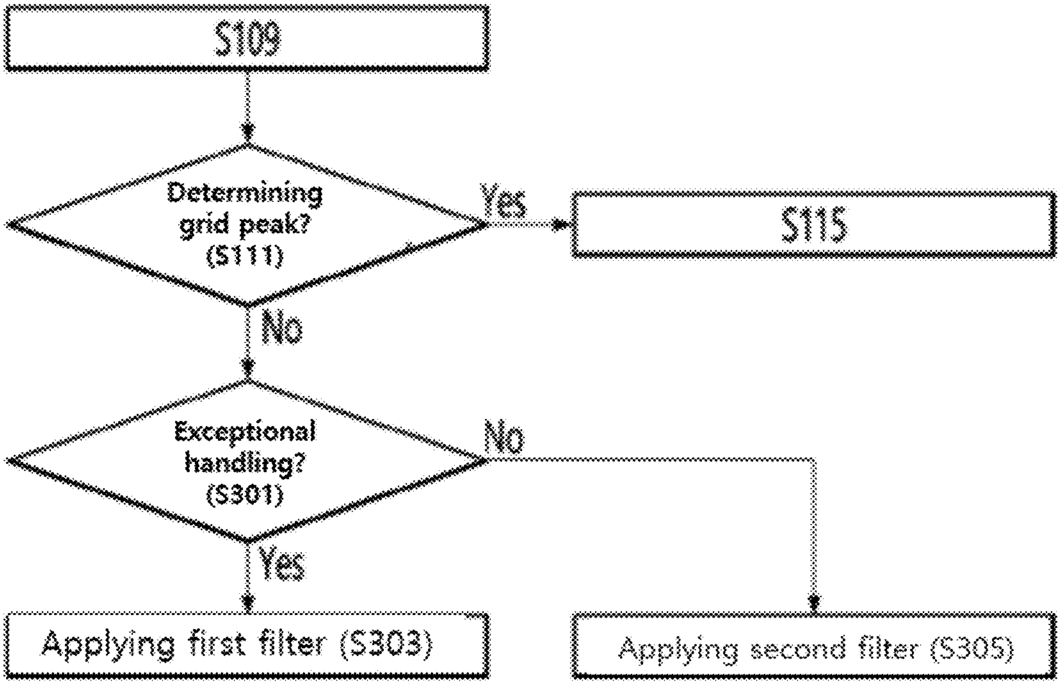

FIGS. 4 to 6 are flowcharts illustrating an image processing method according to an embodiment of the present disclosure.

FIGS. 4 to 6 are described from the perspective of the image processing device 150 or the processor 160 of the image processing device, but are not limited thereto.

For convenience, FIG. 4 can be referred to as an artifact detection process.

First, referring to FIG. 4, the processor 160 can obtain an X-ray image through the image acquisition device 100 (S101).

The processor 160 can convert the X-ray image obtained in step S101 into the frequency domain (S103).

As described above, for conversion to the frequency domain, as an example, FFT can be used to express an arbitrary input signal by decomposing it into the sum of periodic functions having various frequencies.

Figure 7:
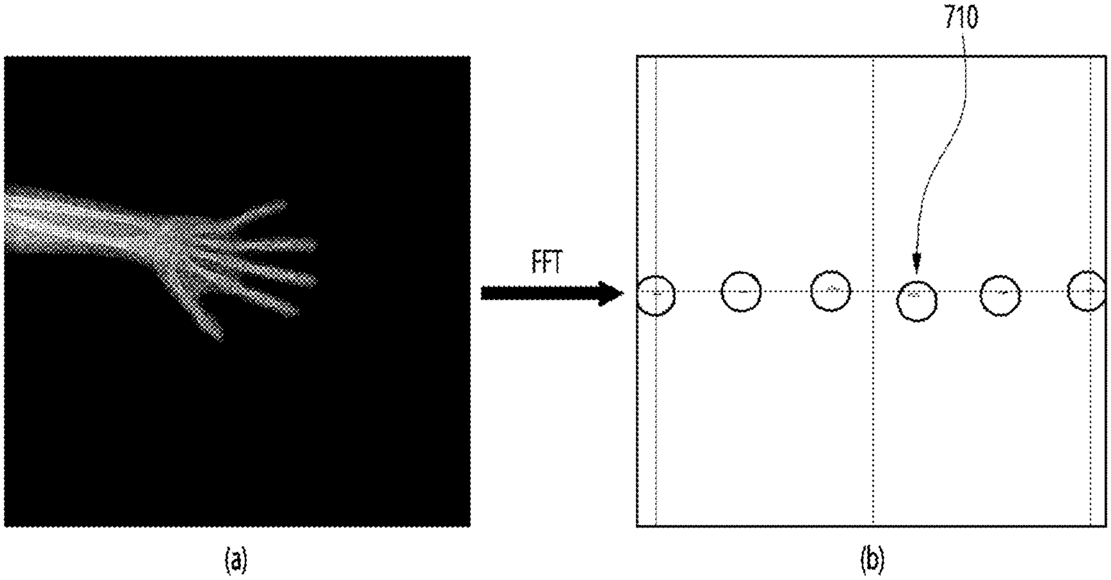
FIG. 7, including (a) and (b), is a diagram illustrating the conversion of an original X-ray image into a frequency domain according to an embodiment of the present disclosure.

Therefore, when FFT is applied to the X-ray image obtained according to the present disclosure, peaks 710 appear periodically as shown in (b) of FIG. 7. Referring to (b) of FIG. 7, 710 (circle) corresponds to the part where the grid line artifact expressed in the spatial domain is expressed in the frequency domain, that is, the grid peak.

The processor 160 can detect grid direction information from the image data that is converted to the frequency domain in step S103 (S105).

Detecting such grid direction information is to analyze the size and location of the grid peak and determine where the grid peak is distributed in the frequency domain. According to an embodiment, the subsequent detection process can be performed only for the region determined to be in the grid direction. In other words, regions that do not correspond to grid peaks can be processed so that the suppression process described later is not performed. The region that does not correspond to the grid peak can include, for example, a region generated in the frequency domain due to a ruler.

In the case of X-ray images transformed into the frequency domain from the raw data, it may be necessary to detect the grid direction information. If such grid direction detection is not performed, it can affect the original image, i.e., the X-ray image in the spatial domain before transformation. Consequently, when performing inverse transformation (or retransformation) to obtain the damaged X-ray image at step S203 of the method described later in section 5, after frequency domain transformation.

For example, (a) of FIG. 8 is an original X-ray image including the ruler 810, and (b) of FIG. 8 is a frequency domain conversion image regarding an original X-ray image including the ruler 810 of (a) of FIG. 8.

Referring to (b) of FIG. 8, unlike (b) of FIG. 7, for example, it can be seen that regions exist in both the vertical and horizontal directions. In this case, it is desirable that the processor 160 suppresses grid artifacts, that is, the grid peak region, but does not suppress the ruler region, as described above.

Therefore, the processor 160 should be able to identify which of the vertical and horizontal directions in (b) of FIG. 8 is a grid peak region resulting from the grid and which is a region resulting from the ruler. This is because only then can the processor 160 perform suppression just on the grid peak region.

As such, in the present disclosure, to avoid processing errors due to suppression of the region caused by the ruler rather than the grid peak region, grid direction information is detected and only the grid peak region is removed to prevent or minimize loss of the original image. On the other hand, performing such an operation is not only efficient because, for example, the grid detection process is performed only for the region determined in the grid direction, saving resource consumption and reducing the time required compared to the case where the grid detection process is performed for the entire region. In addition, it can increase the reliability of grid artifact processing.

In the present disclosure, the grid direction detection can be processed as follows. Meanwhile, the following formula can be used for such a processing.

First, the processor 160 can calculate MaxVal_horizontal and MaxVal_vertical.

In this case, the following equation 1 can be referred to.

MaxVal_horizontal=max(Peak_ratio($i,j$)) on the axis of horizontal direction

MaxVal_vertical=max(Peak_ratio($i,j$)) on the axis of vertical direction [Equation 1]

In the above, Peak_ratio(i,j) can represent, for example, the result of calculating the ratio between the grid peak size at location (i,j) and the grid peak size in the surrounding local region (N×N). Therefore, as the value is larger, it can be identified that the grid peak has a relatively larger value compared to the surrounding region.

Meanwhile, in the above, (i,j) can represent pixel coordinates in the corresponding image.

Next, the shape of the peak that appears due to the ruler can be excluded from the grid peak region. In this case, Equation 2 below can be referred to.

$N$_peak_1=the number of the peak appearing periodically across low to high frequencies $N$_peak_2=the number of the peak distributed in the low-frequency range among $N$_peak_1

If ($N$_peak_1≥$Th$1 and $N$_peak_2≥$Th$2), it is determined that there are peaks along a corresponding axis by the ruler in the image. [Equation 2]

Finally, the grid peak direction can be identified. In this case, Equation 3 below can be referred to.

MaxDirection_value=max(MaxVal_horizontal and MaxVal_vertical) [Equation 3]

The direction in which the MaxDirection_value value is large can be determined as the grid peak region.

However, the above equations and processing processes are not limited to the above-described content. For example, the processor 160 can detect and process the grid peak region based on learning results through an artificial intelligence learning model.

The processor 160 can detect peak shape information from the image data converted to the frequency domain in step S103, based on the grid direction information detected in step S105 (S107).

The grid peak shape detection method can select a grid peak candidate region through grid peak information.

The processor 160 can select (or detect) a grid peak candidate region based on the grid direction information and peak shape information detected through steps S105 and S107, respectively (S109).

The processor 160 can determine whether the grid peak candidate region selected through step S109 is a grid peak (S111).

Before explaining the grid peak determination method, as described above, the grid peak shown by the ruler can be determined to be a grid peak based on the above-described grid peak direction information and thus not removed. Therefore, the grid peak shown by the ruler can be excluded from the grid peak candidate group. In this regard, the above-mentioned grid direction determination can be referred to, and misdetection can be prevented or accuracy can be improved by making redundant judgments.

Regarding determining whether a grid peak exists, the equations and explanations below can be used.

$N$_peak_1=the number of the peak appearing periodically across low to high frequencies $N$_peak_2=the number of the peak distributed in the low-frequency range among $N$_peak_1

If ($N$_peak_1≥$Th$3 and $N$_peak_2≥$Th$4), it is determined that there are peaks along a corresponding axis by the ruler in the image. [Equation 4]

In addition, the processor 160 can further refer to the following equations and explanations or use it instead of the above-described method to determine whether there is a grid peak.

To determine whether there is a grid peak, the processor 160 can analyze peak position (frequency), peak intensity (Peak magnitude), and peak shape (elongation ratio).

That is, the processor 160 can determine whether a grid peak exists based on the analysis of at least one of the peak positions, peak intensity, and peak shape information in addition to the above-described peak direction information.

In the above, the positions of the peak indicates the frequency at which the peak are located in the frequency domain, and the closer it is to a high-frequency, the more weight can be assigned to determine it as a grid peak.

In the above, the shape of the peak calculates the elongation ratio, and if the calculated elongation ratio is greater than or equal to a threshold value, it cannot be judged as a grid peak.

In this case, the following equation can be used.

Peak_ratio($i,j$)>$Th$5

Max_Image_original=max(Image_original($i,j$))

Mean_Image_original(Image_original($i,j$) [Equation 5]

The processor 160 can first detect all (i,j) positions that satisfy the condition that the Peak_ratio(i,j) exceeds Th5 and determine them as peak candidates.

The processor 160 can calculate Max_Image_original, which is the maximum value, and Mean_Image_original, which is the average value, at the detected position.

In the above, Image_original(i,j) can represent the value at the (i,j) position in the image converted from the original image to the frequency domain.

Count=(Image_original($i,j$)>Mean_Image_original($i,j$)) [Equation 6]

If (Count≤Th6 and Image_original (i,j)<Th7), there exclude it from the candidate group.

Next, the processor 160 can calculate the number of pixels that satisfy the condition of Equation 6 for the peak candidate group region determined referring to Equation 5.

If the calculated number of pixels is less than Th7, the processor 160 can exclude the corresponding peak candidate group region from the candidate group.

Meanwhile, the processor 160 can exclude the maximum value and exclude other values from the candidate group through analysis of the local region throughout the image.

The processor 160 can calculate the elongation rate for each peak shape.

The processor 160 can exclude it from the candidate group if the calculated elongation rate for the target peak shape exceeds Th8.

The processor 160 can form a peak map based on the remaining candidates through the above-described process.

If, as a result of the determination in step S111, the peak candidate region does not correspond to a grid peak, the processor 160 can exclude it (S113).

As a result of the determination in step S111, the processor 160 can exclude regions that do not correspond to grid peaks and form a peak map based on the remaining grid peak candidate regions (i.e., regions determined to be grid peaks) (S115.)

However, in step S105 in FIG. 4, for example, when the ruler 810 shown in (a) of FIG. 8 is included, data in the frequency domain of the obtained X-ray image is similar to in (b) of FIG. 8. Since they can appear together, it can be effective for distinguishing them from grid artifacts. Therefore, basically, S105 of FIG. 4 can be performed, but for example, if it is known in advance that the ruler 810 is not included in the obtained X-ray image, step S105 cannot be performed.

According to the artifact detection process shown in FIG. 4 described above, the processor 160 refers to the position, intensity, elongation rate, etc. of the peak in the analysis during the automatic grid direction recognition process and the grid peak determination process to prevent grid misdetection or grid detection performance can be improved by minimizing it.

Next, steps of FIG. 5 can be described as an artifact suppression or filtering process, which involves dealing with the detected artifacts following the artifact detection process shown in the aforementioned FIG. 4.

According to the artifact suppression process shown in FIG. 5, the processor 160 can provide a robust result through a double filter structure and minimizing artifacts by adaptively changing the kernel size based on peak information.

The processor 160 can determine a kernel size based on the shape information of the grid peak and determine a filter type according to the determined kernel size to perform filtering.

If the kernel size determined based on the shape information of the grid peak is greater than or equal to a threshold, the processor 160 can perform filtering using n Gaussian notch filters (where n is a natural number of 2 or more).

According to an embodiment, processor 160 can perform filtering using a single Gaussian notch filter when the kernel size determined based on the shape information of the grid peak is less than a threshold.

The processor 160 can perform filtering by determining the kernel size and filter type for each peak.

The processor 160 can increase the filtering strength as it approaches the high-frequency region, and can decrease the filtering strength as it approaches the low-frequency region.

In FIG. 5, a flowchart is illustrated to explain the artifact suppression process, that is, the process of processing detected artifacts, that is, grid peaks.

Referring to FIG. 5, the processor 160 can perform filtering on the X-ray image data converted to the frequency domain based on the peak map formed in step S115 (S201).

The processor 160 can convert the X-ray image data in the frequency domain filtered in step S201 into X-ray image data in the spatial domain (S203).

The processor 160 can control the X-ray image data inversely converted to the spatial domain through step S203 to be output to the user through the display 180 as a result (S205).

The processor 160 can perform filtering based on the peak map formed in FIG. 4. For example, such a filtering can be referred to as Adaptive Band stop filtering to respond to, or suppress, various types of grid peaks.

In other words, the processor 160 can adaptively use the kernel size based on the information of the peak map to respond to various types of grid peaks.

According to an embodiment, the processor 160 can respond to individual grid peaks by adjusting the kernel size shown in FIG. 10.

According to another embodiment, the processor 160 can apply a different kernel size depending on the location of the grid peak. In this case, the position of the grid peak is based on the image converted to the frequency domain. For example, referring to (a) of FIG. 9, based on the center point 910 where many images of actual human body shapes are gathered, the closer to the center point 910 the low-frequency region, and conversely, the farther at the center point 910 The further away you are, the higher the frequency range. Accordingly, the processor 160 can set the kernel size for a grid peak located in a relatively low-frequency region to be different from the kernel size for a grid peak located in a high-frequency region. For example, as grid peaks are located in the high-frequency region, they are removed relatively strongly because they do not significantly affect the original image, and conversely, as grid peaks are located in the low-frequency region, they are removed relatively weakly because they greatly affect the original image, thereby reducing the risk of damage to the original image. This is to prevent or minimize.

Therefore, referring to FIG. 10, a graph of the kernel size for grid peaks located in a low-frequency region can be different from a graph of the kernel size for grid peaks located in a high-frequency region.

Additionally, the processor 160 can set the kernel size differently depending on the size of the grid peak. In this regard, the processor 160 can set different weights depending on the shape of the peak based on the content described above. In this regard, Equation 7 below can be referred to.

[Equation 7]

$$\text{kernel size}=\alpha_{high}*\text{peak}_{magnitude}+\beta_{high}*\text{peak}_{size}+\omega_{peak_{elongation}}(\text{peak}_{location}<Th9) \quad [1]$$

$$\text{kernel size}=\alpha_{low}*\text{peak}_{magnitude}+\beta_{low}*\text{peak}_{size}+\omega_{peak_{elongation}}(\text{peak}_{location}\geq Th9) \quad [2]$$

In calculating the kernel size according to Equation 7, the [1] can be an equation applied to the low-frequency region, and the [2] can be an equation applied to the high-frequency region.

In particular, the processor 160 can respond to various peak shapes through a double filter structure as shown in FIG. 10. For example, an elongated grid peak such as FIG. 9(*b*) can also be responded to through the double filter structure according to the present disclosure. In this case, the processor 160 can remove various types of artifacts by adaptively applying filtering according to the grid peak, such as setting the filtering intensity to a weak level by partially adjusting the intensity because there is a risk of damage to the original in regions close to the signal region.

According to an embodiment, the processor 160 cannot always apply a double filter but can use only one filter structure shown in FIG. 10. In particular, the problem is not the shape or size of the general grid peak as shown in (b) of FIG. 9, that is, for the abnormal grid peak, the processor 160 can use a single filter if the abnormal grid peaks based on the above-mentioned deformed peak map before applying filtering are not included.

In this regard, although not described in the peak map forming method, the processor 160 can display abnormal grid peaks such as those described above so that they can be separately identified when forming the peak map. Referring to FIG. 9, the shape, size, and location of abnormal grid peaks can be displayed on the peak map, or depending on the embodiment, only the presence or absence of abnormal grid peaks can be displayed. Accordingly, when only the presence or absence of a grid peak is indicated, the processor 160 can perform a filtering operation using a double filter as shown in FIG. 10. In this case, the kernel size for removing the abnormal grid peak can be calculated as an arbitrary value. Here, the arbitrary value can be referred to as any one of the kernel size history data set in the filter in the same or similar case, an average value, a default value, or a value determined by considering the kernel size calculated for another filter.

According to another embodiment, the processor 160 does not apply a double filter from the beginning, but can set to apply a filter having a different kernel size or a double filter after viewing the image in inverse transform as described above after applying one filter first as shown in the graph of FIG. 10. That is, the processor 160 can selectively choose a filter.

In this way, by performing a double Gaussian operation, the processor 160 can set a different gain strength of the filter depending on the region where the grid is located, and control it to be applied only to a necessary range.

Finally, the processor 160 can inversely transform or re-transform the image into the spatial domain. That is, the processor 160 can perform IFFT on the frequency components from which the grid peaks in (a) of FIG. 11 has been removed to generate a final result image as shown in (b) of FIG. 11.

Respective views (a) and (c), illustrate input X-ray images, and respective views (b) and (d) of FIG. 12 illustrate the final result images post-processed according to the present disclosure. That is, the images shown in FIGS. 12(*b*) and 12(*d*) can be the images that are ultimately provided to the user (i.e., the reader) through the display 180.

Meanwhile, FIG. 6 can be another embodiment after selecting the grid peak candidate region in step S109 of FIG. 4 described above.

After the grid peak candidate region is selected as shown in FIG. 4 described above, the processor 160 can determine whether each grid peak candidate region is a grid peak (S111).

If the determination results in step S111 correspond to a grid peak, the processor 160 can leave the corresponding grid peak region (or mark it) and refer to it when forming a peak map later (S115).

However, if it is determined in step S111 that it does not correspond to a grid peak, the processor 160 can determine whether exception handling is necessary again (S301).

Although FIG. 6 illustrates determining whether exception handling is necessary when it is not determined to be a grid peak, but is not limited to thereto. Accordingly, the processor 160 can determine whether exception handling is necessary even when it is determined that it corresponds to a grid peak as a result of the determination in step S111.

Here, the exception handling can be represented to process abnormal point(s), for example, the first point 920 and the second point 930 shown in (b) of FIG. 9, detected with characteristics different from the peak 710 shown in (b) of FIG. 7 or the peak 820 shown in (b) of FIG. 8.

According to an embodiment, another point 830 in (b) of FIG. 8 can also be subject to such an exception handling.

Referring again to FIG. 6, if exception handling is necessary as a result of the determination in step S301, the processor 160 can perform filtering operation by applying the first filter (S303).

On the other hand, if exception handling is not necessary as a result of the determination in step S301, the processor 160 can perform a suppression (or filtering) by applying a second filter (S305).

In this case, the first filter can be, for example, a dual filter shown in FIG. 10.

Meanwhile, the second filter can be, for example, a filter using only one of the dual filters shown in FIG. 10.

Meanwhile, in the present disclosure, as an example, a Gaussian notch filter is used for filtering. In particular, the notch filter is for an adaptive band stop filtering method, and as shown in FIG. 10, artifacts can be stably eliminated with prevented deterioration from the original X-ray image or minimized the deterioration of the original X-ray image, regardless of a peak form (or shape), through first filter 1010 and second filter 1020 shown in FIG. 10.

In other words, through the double filter shown in FIG. 10, the processor 160 can perform filtering abnormal artifacts 920 and 930 in (b) of FIG. 9, as well as (b) of FIG. 7, or (b) of FIG. 8.

In the graph shown in (a) of FIG. 9, the closer to the center 910, the low-frequency region can be represented, and the farther from the center, the high-frequency region can be represented.

Concerning this, although the abnormal artifacts 920 and 930 in (b) of FIG. 9 are located in the high-frequency region, but are not limited thereto. The processor 160 can determine whether the peak is a normal peak or an abnormal artifact based on the shape of the peak. For example, the abnormal artifacts 920 and 930 have a relatively longer shape than the general peak shown in FIG. 7(*b*). As described above, this can be determined based on the elongation ratio.

According to an embodiment, the post-processing process according to the present disclosure, that is, the processes of FIGS. 4 to 6, can be repeated a predetermined number of times for one input X-ray image. During the iterative process, the filter kernel size, etc. applied to each round can be different.

FIG. 12 is a diagram illustrating an original X-ray image and a post-processed image according to an embodiment of the present disclosure.

FIGS. 12(*a*) and 12(*c*) illustrate an original X-ray image, and FIGS. 12(*b*) and 12(*d*) respectively illustrate an X-ray image post-processed according to an embodiment according to the present disclosure.

Although the present specification has been described using X-ray images as an example, it is not necessarily limited thereto, and can be applied to Computerized Tomography (CT) images, etc. in the same or similar manner. Moreover, the present disclosure can be applied not only to the medical field but also to various industrial fields that process artifacts using X-rays.

The above description is merely an illustrative explanation of the technical idea of the present invention, and various modifications and variations can be made by those skilled in the art without departing from the essential characteristics of the present invention.

Accordingly, the embodiments disclosed in the present invention are not intended to limit the technical idea of the present invention, but are for illustrative purposes, and the scope of the technical idea of the present invention is not limited by these embodiments.

The scope of protection of the present invention shall be interpreted in accordance with the claims below, and all technical ideas within the equivalent scope shall be construed as being included in the scope of rights of the present invention.

INDUSTRIAL APPLICABILITY

According to the image processing device according to the present disclosure, the accuracy of X-ray image processing is improved by preventing or minimizing erroneous detection of grid artifacts, thereby improving the readability and diagnostic accuracy of the X-ray image, so it can be used industrial applicability.

What is claimed is:

1. An image processing method, comprising:
obtaining an X-ray image;
converting the obtained X-ray image into a frequency domain;
detecting peak shape information from the converted X-ray image in the frequency domain;
selecting a peak candidate region based on the detected peak shape information;
determining whether each selected peak candidate region is a grid peak and generating a peak map;
filtering the converted X-ray image based on the generated peak map;
converting the filtered X-ray image in the frequency domain into a spatial domain; and
generating a domain converted X-ray image in the spatial domain in which a grid artifact is suppressed while a ruler image is preserved based on detecting grid direction information and selectively filtering only the grid peak identified based on the grid direction information, in order to minimize loss of the X-ray image,
wherein the filtering of the converted X-ray image is performed using n Gaussian notch filters, where n is a natural number of 2 or more, when a determined kernel size based on the peak shape information of a grid is greater than or equal to a threshold to generate the filtered X-ray image, and
wherein the filtering of the converted X-ray image is performed using a single Gaussian notch filter when the determined kernel size based on the peak shape information of the grid is less than the threshold to generate the filtered X-ray image.

2. The image processing method according to claim 1, wherein regions including peaks exceeding predefined shapes and sizes based on the detected peak shape information are excluded from the peak candidate region.

3. The image processing method of claim 2, further comprising detecting peak direction information from the converted X-ray image in the frequency domain.

4. The image processing method of claim 3, wherein the determination of whether there is the grid peak is performed based on the peak direction information.

5. The image processing method of claim 4, wherein the peak direction information includes direction information on the grid artifact and direction information by the ruler image.

6. The image processing method of claim 5, wherein, based on the peak direction information, when a peak by the ruler image is detected, the peak by the ruler image is excluded from the peak map.

7. The image processing method of claim 6, wherein the determination of whether there is the grid peak is performed based on analysis of at least one of a peak location, peak intensity, and peak shape information.

8. The image processing method of claim 7, wherein a position of a peak indicates a frequency at which the peak is located in the frequency domain, and the closer the peak is to a predetermined frequency, more weight is given to determine the peak as the grid peak.

9. The image processing method of claim 7, wherein a shape of the peak is not determined to be the grid peak when an elongation rate is calculated, and when the calculated elongation rate is greater than or equal to a threshold value.

10. The image processing method of claim 7, wherein, in the filtering of the converted X-ray image, a kernel size is determined based on the peak shape information of the grid, and a filter type is determined according to the determined kernel size.

11. The image processing method of claim 10, wherein, in the filtering of the converted X-ray image, the kernel size and filter type for each peak are determined.

12. The image processing method of claim 10, wherein, in the filtering of the converted X-ray image, a filtering strength increases closer to a high-frequency region and the filtering strength decreases closer to a low-frequency region.

13. An image processing device, comprising:
a data receiver configured to obtain an X-ray image;
a first converter configured to convert the obtained X-ray image into a frequency domain;
a data processor configured to detect peak shape information from the converted X-ray image in the frequency domain, select a peak candidate region based on the detected peak shape information, determine whether each selected peak candidate region is a grid peak and generate a peak map, and filter the converted X-ray image based on the generated peak map;
a second converter configured to convert the filtered X-ray image in the frequency domain into a spatial domain; and
a controller configured to control the image processing device to generate a domain converted X-ray image in the spatial domain in which a grid artifact is suppressed while a ruler image is preserved by detecting grid direction information and selectively filtering only the grid peak identified based on the grid direction information, in order to minimize loss of the X-ray image,
wherein the filtering of the converted X-ray image by the data processor is performed using n Gaussian notch filters, where n is a natural number of 2 or more, when a determined kernel size based on the peak shape information of a grid is greater than or equal to a threshold to generate the filtered X-ray image, and
wherein the filtering of the converted X-ray image by the data processor is performed using a single Gaussian notch filter when the determined kernel size based on the peak shape information of the grid is less than the threshold to generate the filtered X-ray image.

14. The image processing device according to claim 13, wherein regions including peaks exceeding predefined shapes and sizes based on the detected peak shape information are excluded from the peak candidate region.

15. The image processing device according to claim 14, wherein the data processor is further configured to detect peak direction information from the converted X-ray image in the frequency domain.

16. The image processing device according to claim 15, wherein the peak direction information includes direction information on the grid artifact and direction information by the ruler image.

17. The image processing device according to claim 16, wherein, based on the peak direction information, when a peak by the ruler image is detected by data processor, the peak by the ruler image is excluded from the peak map.

18. An image processing method, comprising:
converting an X-ray image into a frequency domain;

detecting peak shape information from the converted X-ray image in the frequency domain;

selecting a peak candidate region based on the detected peak shape information;

determining whether each selected peak candidate region is a grid peak and generating a peak map;

filtering the converted X-ray image based on the generated peak map;

excluding a grid artifact from the peak map of the filtered X-ray image; and generating a domain converted X-ray image in a spatial domain in which the grid artifact is suppressed while a ruler image is preserved by detecting grid direction information and selectively filtering only the grid peak identified based on the grid direction information, in order to minimize loss of the X-ray image, wherein the filtering of the converted X-ray image is performed using n Gaussian notch filters, where n is a natural number of 2 or more, when a determined kernel size based on the peak shape information of a grid is greater than or equal to a threshold to generate the filtered X-ray image, and wherein the filtering of the converted X-ray image is performed using a single Gaussian notch filter when the determined kernel size based on the peak shape information of the grid is less than the threshold to generate the filtered X-ray image.

* * * * *